United States Patent [19]

Wingender et al.

[11] Patent Number: 5,455,329
[45] Date of Patent: Oct. 3, 1995

[54] DNA SEQUENCES CODING FOR PTH VARIANTS, PTH VARIANTS, EXPRESSION VECTOR, BACTERIAL HOST, USE AND THERAPEUTIC COMPOSITION

[75] Inventors: Edgar Wingender; Heiko Mielke; Gisela Bercz-Timm; Klaus Dieter Schlüter; Hubert Mayer, all of Braunschweig, Germany

[73] Assignee: Gesellschaft fur Biotechnologische Forschung mbH (GBF), Braunschweig, Germany

[21] Appl. No.: 968,165

[22] Filed: Oct. 29, 1992

Related U.S. Application Data

[62] Division of Ser. No. 573,219, Aug. 16, 1990.

[30] Foreign Application Priority Data

Feb. 23, 1989 [DE] Germany .......................... 39 05 606.6

[51] Int. Cl.[6] ...................... C07K 14/635; C07K 14/575; C12N 15/16; A61K 38/29
[52] U.S. Cl. ............................................. 530/324; 530/300
[58] Field of Search ................................... 530/324, 307, 530/300; 435/172.3; 514/12

OTHER PUBLICATIONS

Chorev, M. et al, *Biochemistry* 29:1580–1586 (Feb. 13, 1990).

Rosenblatt, M. et al. *J. Biol. Chem.* 251:159–164 (1976).

*Primary Examiner*—Robert A. Wax
*Assistant Examiner*—Dian C. Jacobson
*Attorney, Agent, or Firm*—Kane, Dalsimer, Sullivan, Kurucz, Levy, Eisele and Richard

[57] ABSTRACT

The invention relates to DNA sequences coding for PTH variants, to PTH variants, expression vectors, bacterial hosts, uses and therapeutic compositions.

11 Claims, No Drawings

5,455,329

DNA SEQUENCES CODING FOR PTH VARIANTS, PTH VARIANTS, EXPRESSION VECTOR, BACTERIAL HOST, USE AND THERAPEUTIC COMPOSITION

This is a Division of copending application Ser. No. 573,219, filed Aug. 16, 1990.

BACKGROUND OF THE INVENTION

1. Field of the Invention

The invention related to analogs of parathyroid hormone.

2. Brief Description of Related Art.

Parathyroid hormone (PTH) regulates the level of calcium in blood plasma by exerting, inter alia, anabolic and catabolic effects on the skeleton and also by promoting calcium re-absorption by the kidneys. There is reason to believe that the bone-building effect of PTH can be exploited for the clinical treatment of osteoporosis; see J. Bone Mineral Res., 1 (1987 ) 377–382.

There are also indications that the multiple functions of PTH are exerted by different regions of the hormone molecule. For example, it has been found that the N-terminal 34 amino acids mediate the binding of the hormone to its kidney cell receptor with subsequent stimulation of adenylate cyclase (see Adv. Prot. Chem., 32 (1982) 323–395) but that a mitogenic effect originates from the central region sequence 28–48 (see DE-A-37 25 319.0) which effect is not mediated by adenylate cyclase but possibly by protein kinase C. It would therefore seem attractive to modulate individual hormone effects by controlled variation of the amino acid sequence of PTH or of PTH fragments and thus possibly to reduce the catabolic activity of the hormone or increase its anabolic activity.

With regard to the prior art, reference should also be made to U.S. Pat. Nos. 4,086,196 and 4,423,037 and John et al., in Adv. Prot. Chem., 32 (1982) 323.

SUMMARY OF THE INVENTION

For the above purpose, according to the invention a DNA sequence is provided that codes for a variant of PTH(1–84), in which one or two amino acids is/are exchanged for another amino acid in the region of positions 1 to 27, and which is optionally lengthened N-terminally (position +1) by one or two amino acids and is optionally also shortened C-terminally (position +84) by one or more amino acids or is optionally shortened C-terminally (position +84) by one or more amino acids, the amino acids coded by the DNA sequence not being arranged in an order that occurs in bPTH, pPTH, rPTH, cPTH or hPTH.

According to a further embodiment, a DNA sequence is provided that codes for a variant of PTH(1–84), in which one or two amino acids is/are exchanged for another amino acid in the region of positions 28 to 31, and which is optionally lengthened N-terminally (position +1) by one or two amino acids and is optionally also shortened C-terminally (position +84) by one or more amino acids or is optionally shortened N-terminally (position +1) and/or C-terminally (position +84) by one or more amino acids, the amino acids coded by the DNA sequence not being arranged in an order that occurs in bPTH, pPTH, rPTH, cPTH or hPTH.

According to a further embodiment, a DNA sequence is provided that codes for a variant of PTH(1–84), in which one or two amino acids is/are exchanged for another amino acid in the region of positions 32 to 34, except that tyrosine may not appear at position 34, and, further, which is optionally lengthened N-terminally (position +1) by one or two amino acids and is optionally also shortened C-terminally (position +84) by one or more amino acids or is optionally shortened N-terminally (position +1) and/or C-terminally (position +84) by one or more amino acids, the amino acids coded by the DNA sequence not being arranged in an order that occurs in bPTH, pPTH, rPTH, cPTH or hPTH.

According to a further embodiment, a DNA sequence is provided that codes for a variant of PTH(1–84), in which one or two amino acids is/are exchanged for another amino acid in the region of positions 30 to 34, and which is optionally lengthened N-terminally (position +1) by one or two amino acids and is optionally also shortened C-terminally (position +84) by one or more amino acids or is optionally shortened N-terminally (position +1) and/or C-terminally (position +84) by one or more amino acids, the totality of the amino acids coded by the DNA sequence not being arranged in an order that occurs in bPTH, pPTH, rPTH, cPTH or hPTH.

According to a further embodiment, a DNA sequence is provided that codes for a variant of PTH(1–84), in which (a) the region of positions 28 to 34 and especially 30 to 34 is unchanged or (b) one or two amino acids is/are exchanged for another amino acid in the region of positions 28 to 34 and especially 30 to 34 and, in addition to (a) or (b), one or two amino acids is/are exchanged for another amino acid outside the region of positions 28 to 34 or 30 to 34, and which is optionally lengthened N-terminally (position +1) by one or two amino acids and is optionally also shortened C-terminally (position +84) by one or more amino acids or is optionally shortened N-terminally (position +1) and/ or C-terminally (position +84) by one or more amino acids, the totality of the amino acids coded by the DNA sequence not being arranged in an order that occurs in bPTH, pPTH, rPTH, cPTH or hPTH.

The DNA sequence preferably codes for a PTH variant whose N-terminus is lengthened by proline. Also preferred are hPTH, bPTH, pPTH, rPTH and cPTH variants. As regards the numbering of the DNA sequences, 1 denotes the first nucleotide of the first PTH codon so that the numbers to be found in the following Table 1 denote the position of the first nucleotide shown in relation to the first nucleotide of the first PTH codon.

According to a further embodiment, the invention relates also to PTH variants that are coded by one of the above-described DNA sequences, and especially variants of human (h), bovine (b), porcine (p), rat (r) and canine (c) PTH.

DETAILED DESCRIPTION OF THE PREFERRED EMBODIMENTS OF THE INVENTION

The PTH variants according to the invention can be formally classified in the following four groups.

Group 1: conservative amino acid exchanges in positions 27 and 29 that maintain the stimulation both of adenylate cyclase and of DNA synthesis ("functional PTH equivalents"); Examples: Q29N; K27R.

Group 2: non-conservative amino acid exchanges (variations with charge reversal or cancellation, change of hydrogen bridges, reversal of hydrophobicity) in regions 29 to 31 or 33 to 34 and also exchanges in position 32 that result in a significant reduction in the stimulation of DNA synthesis and in a substantial retention of the effect on adenylate cyclase; Examples Q29A, H32L, H32K, H32R.

Group 3: non-conservative amino acid exchanges (as defined above) in region 1 to 27 that result in a significant reduction in adenylate cyclase stimulation and in some cases increase DNA synthesis or leave it unaffected. Examples of increase in DNA synthesis: E4R, E4R/R20E, K13P, K27L; Example of unaffected DNA synthesis: R20E.

Group 4: non-conservative amino acid exchanges in region 1 to 27 that maintain the stimulation of adenylate cyclase but reduce that of DNA synthesis; Example: L11K.

Finally, the invention relates to hybrid peptides that include a PTH variant according to the invention, to expression vectors for the expression of the proteins according to the invention, bacterial hosts, such as *E. coli*, for the expression vectors, the use of the DNA sequences for the preparation of the peptides according to the invention, and therapeutic compositions that contain those peptides. DE-A-37 25 319.0 and DE-A-37 25 320.4 are relevant prior art.

The invention is explained in more detail below by an Example and two Tables.

EXAMPLE

The expression plasmid pEX-pPTH of DE-A-37 25 319.0 was used as starting material. A BamHI/SstI fragment of this plasmid 123 base pairs long was recloned into phage vector M13mp18. Using this phage vector and using synthetic oligonucleotides, the mutants listed in Table 1 were prepared in accordance with the gapped-duplex-method (Methods Enzymol., 100 (1983) 468–500).

After back-cloning the mutated PTH partial genes into the expression vector, the corresponding variant Cro-β-galactosidase-hPTH-fusion proteins were expressed, purified and cleaved; the PTH variants freed in that manner were purified in accordance with DE-A-37 25 319.0 and DE-A-37 25 320.4. Purification by means of carboxymethylcellulose was carried out batchwise. Subsequent purification by reversed-phase HPLC yielded homogeneous material.

The PTH variants so obtained were tested for their ability to stimulate adenylate cyclase in isolated membranes of porcine adrenal cortices in an in vitro test according to Mohr and Hesch (Biochem. J., 188 (1980) 649–656).

They were also tested for their ability, according to DE-A-37 25 319.0 and DE-A-37 25 320.4, to increase the DNA synthesis of embryonal chicken chondrocytes.

The results obtained are compiled in Table 2.

| Materials | |
|---|---|
| pEX | Genofit Heidelberg |
| M13mp18 | GIBCO BRL |
| hPTH gene | P 33 12 928.2 |
| bPTH gene | PNAS, 78 (1981) 7365 |
| pPTH gene | Nucleic Acids Res., 15 (1987) 6740 |
| rPTH gene | Nucleic Acids Res., 15 (1987) 6740 |
| cPTH gene | J. Bone Mineral. Res., 3 (Suppl. 1) (1988) Poster No. 309 |

The PTH genes mentioned can be prepared using peptide synthesis apparatus.

TABLE 1

Mutations in the hPTH gene and resulting PTH variants

| Name | DNA sequence | AA exchange | |
|---|---|---|---|
| E4R | AGT AGA ATT 28 | Glu(4) | -> Arg(4) |
| L11K | AAC AAG GGA 31 | Leu(11) | -> Lys(11) |
| G12A | CTC GCG AAA | Gly(12) | -> Ala(12) |
| G12P | CTC CCG AAA 34 | Gly(12) | -> Pro(12) |
| K13P | GGC CCA CAT | Lys(13) | -> Pro(13) |
| K13S | GCC TCC CAT | Lys(13) | -> Ser(13) |
| K13L | GGC CTG CAT | Lys(13) | -> Leu(13) |
| G12N, K13S | AAT TCC CAT 55 | Gly(12), Lys(13) -> Asn(12), Ser(13) | |
| R20E | GAG GAA GTA 7     55 | Arg(20) | -> Glu(20) |
| E4R, R20E | AGT AGA ATT..GAG GAA GTA 76 | Glu(4) Arg(20) -> Arg(4), Glu(20) | |
| K27L | AAG CTT CTG | Lys(27) | -> Leu(27) |
| K27R | AAG CGT CTG 82 | Lys(27) | -> Arg(27) |
| Q29A | CTG GCA GAT | Gln(29) | -> Ala(29) |
| Q29N | CTC AAC GAT | Gln(29) | -> Asn(29) |

TABLE 1-continued

Mutations in the hPTH gene and resulting PTH variants

| Name | DNA sequence | AA exchange | |
|---|---|---|---|
| | 91 | | |
| H32L | GTA CTC AAT | His(32) | -> Leu(32) |
| H32R | GTG CGC AAT | His(32) | -> Arg(32) |
| H32K | GTG AAG AAT | His(32) | -> Lys(32) |
| H32S | GTT TCG AAT | His(32) | -> Ser(32) |

The numbering at the DNA sequences indicates the position of the first nucleotide shown in relation to the first nucleotide of the first PTH codon (=1). The underlined bases have been changed in relation to the recombinant wild type. The position numbers of the exchanged amino acids refer to the first amino acid of human parathyroid hormone ( Ser(1))

TABLE 2

Relative activity of the PTH variants on renal adenylate cyclase and DNA synthesis in chondrocytes

| PTH-variant | Adenylate cyclase (%) | DNA synthesis (%) |
|---|---|---|
| rec-hPTH | 100 | 100 |
| Q29N | 99 | 95 |
| K27R | 90 | 81 |
| Q29A | 104 | 8 |
| H32L | 93 | 11 |
| H32R | 87 | 36 |
| H32K | 85 | 22 |
| L11K | 89 | 21 |
| E4R | 47 | 88 |
| K27L | 35 | 70 |
| E4R, R20E | 20 | 58 |
| K13P | 6 | 88 |
| R20E | 0 | 0 |

All the PTH variants, like the wild type, are lengthened N-terminally by one proline residue. All the activities are relative to that of the recombinant hPTH and indicate the ability of the respective variant to stimulate either cyclase or DNA synthesis beyond the base level.

We claim:

1. A variant of PTH(1–84), in which one or two amino acids are exchanged for another amino acid in the region of positions 1 to 27, and which is lengthened N-terminally (position +1) by one or two amino acids, the amino acids coded by the DNA sequence not being arranged in a sequence that occurs in bPTH, pPTH, rPTH, cPTH or hPTH.

2. A variant of PTH(1–84), in which one or two amino acids are exchanged for another amino acid in the region of positions 28 to 31, and which is lengthened N-terminally (position +1) by one or two amino acids, the amino acids not being arranged in a sequence that occurs in bPTH, pPTH, rPTH, cPTH or hPTH.

3. A variant of PTH(1–84), in which one or two amino acids are exchanged for another amino acid in the region of positions 30 to 34, except that tyrosine may not appear at position 34, and, further which is optionally lengthened N-terminally (position +1) by one or two amino acids, the amino acids not being arranged in a sequence that occurs in bPTH, pPTH, rPTH, cPTH or hPTH.

4. A variant of PTH(1–84) according to claim 3, in which one or two amino acids are exchanged for another amino acid in the region of positions 32 to 34.

5. A variant according to any one of claims 1, 2, 3, 4 which is lengthened N-terminally by proline.

6. A variant of PTH(1–84), in which one or two amino acids are exchanged for another amino acid in the region of positions 1 to 27, and which is shortened C-terminally (position +84) by one amino acid, the amino acids not being arranged in a sequence that occurs in bPTH, pPTH, rPTH, cPTH or hPTH.

7. A variant of PTH(1–84), in which one or two amino acids are exchanged for another amino acid in the region of positions 28 to 31, and which is shortened C-terminally (position +84) by one amino acid, the amino acids not being arranged in a sequence that occurs in bPTH, pPTH, rPTH, cPTH or hPTH.

8. A variant of PTH(1–84), in which one or two amino acids are exchanged for another amino acid in the region of positions 30 to 34, except that tyrosine may not appear at position 34, and, further which is shortened C-terminally (position +84) by one amino acid, the amino acids not being arranged in a sequence that occurs in bPTH, pPTH, rPTH, cPTH or hPTH.

9. A variant of PTH(1–84) according to claim 8, in which one or two amino acids are exchanged for another amino acid in the region of positions 32 to 34.

10. A variant of PTH(1–84), in which one or two amino acids are exchanged for another amino acid in the region of positions 28 to 34 except that tyrosine may not appear at position 34 and, in addition one or two amino acids are exchanged for another amino acid outside the region of positions 28 to 34 and which is optionally shortened N-terminally (position +1) and C-terminally (position +84) by one amino acid, the amino acids not being arranged in a sequence that occurs in bPTH, pPTH, rPTH, cPTH or hPTH.

11. A variant of PTH (1–84) according to claim 10 wherein said region is of positions of 30 to 34.

* * * * *

UNITED STATES PATENT AND TRADEMARK OFFICE
CERTIFICATE OF CORRECTION

PATENT NO. : 5,455,329
DATED : October 3, 1995
INVENTOR(S) : Edgar Wingender, et al.

It is certified that error appears in the above-indentified patent and that said Letters Patent is hereby corrected as shown below:

Col. 1, line 12; "related" should read -- relates --

Col. 4, Table 1, last line; "CTC" should read -- CTG --

Signed and Sealed this

Second Day of April, 1996

Attest:

BRUCE LEHMAN

Attesting Officer

Commissioner of Patents and Trademarks